US008272252B2

(12) United States Patent
Gupta et al.

(10) Patent No.: US 8,272,252 B2
(45) Date of Patent: Sep. 25, 2012

(54) PORE STRUCTURE CHARACTERIZATION OF FILTRATION CARTRIDGES AT SPECIFIC LOCATIONS ALONG CARTRIDGE LENGTH

(75) Inventors: Krishna M. Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 0 days.

(21) Appl. No.: 12/970,768

(22) Filed: Dec. 16, 2010

(65) Prior Publication Data

US 2011/0174057 A1    Jul. 21, 2011

Related U.S. Application Data

(60) Continuation-in-part of application No. 12/558,865, filed on Sep. 14, 2009, now Pat. No. 8,136,387, and a division of application No. 11/548,067, filed on Oct. 10, 2006, now Pat. No. 7,614,279.

(51) Int. Cl.
*G01N 15/08* (2006.01)
*B01D 39/00* (2006.01)

(52) U.S. Cl. .................... 73/38; 210/85; 210/87; 210/90

(58) Field of Classification Search ........ 73/38; 210/85, 210/87, 90
See application file for complete search history.

(56) References Cited

U.S. PATENT DOCUMENTS

| | | | |
|---|---|---|---|
| 3,610,420 A * | 10/1971 | Sampson et al. | ............. 210/490 |
| 4,069,704 A | 1/1978 | Grant, Jr. et al. | |
| 4,223,551 A | 9/1980 | Greve | |
| 4,246,774 A * | 1/1981 | Flesselles et al. | ................ 73/38 |
| 4,332,679 A | 6/1982 | Hengst | |
| 4,341,109 A | 7/1982 | Evans, Jr. | |
| 4,348,887 A | 9/1982 | Lorenz | |
| 4,355,535 A | 10/1982 | Vaughan | |
| 4,471,650 A | 9/1984 | Koch | |
| 4,538,450 A | 9/1985 | Koch | |
| 4,912,964 A * | 4/1990 | Ohtsuki et al. | ................ 73/38 |
| 5,428,987 A | 7/1995 | Rousseau | |
| 6,134,948 A * | 10/2000 | Fuchigami et al. | ............. 73/38 |
| 6,706,189 B2 * | 3/2004 | Rabie et al. | .................. 210/636 |
| 2002/0036163 A1 * | 3/2002 | Miller et al. | ................ 210/248 |

(Continued)

OTHER PUBLICATIONS

Jena and Gupta, Pore Size Distribution in Porous Materials, Proceedings of International Conference Filtration 99, Nov. 3-4, Chicago, INDA, 1999.*

(Continued)

*Primary Examiner* — David Rogers
(74) *Attorney, Agent, or Firm* — Aquilla Patents & Marks PLLC; Thomas T. Aquilla

(57) ABSTRACT

A method for determining pore structure characteristics of a filtration cartridge includes the steps of placing a porometry test location isolating device in sealing contact with the filtration cartridge at a desired test location, increasing the porometer test gas pressure until the test gas flows through the cartridge at the test location, measuring the flow rate of the test gas through the test location as a function of differential pressure, reducing the test gas pressure to atmospheric pressure, wetting the test location with a wetting liquid, increasing the test gas pressure again until the test gas flows through the cartridge at the test location, measuring differential gas pressure and gas flow rates through the test location, and converting the measured gas flow rates and differential pressures into through pore throat diameters, largest through pore throat diameter, mean flow through pore throat diameter, pore distribution, and gas permeability of the cartridge.

17 Claims, 2 Drawing Sheets

U.S. PATENT DOCUMENTS

2002/0189988 A1* 12/2002 Alexander et al. ............ 210/169
2005/0115879 A1* 6/2005 Kochergin et al. ............ 210/193
2007/0001324 A1* 1/2007 Cote et al. .................. 261/122.1
2007/0221584 A1* 9/2007 Ruprecht ...................... 210/767

OTHER PUBLICATIONS

Jena and Gupta, Characterization of Pore Structure of Filtration Media, Fluid/Particle Separation Journal, vol. 14, No. 3, 2002, pp. 227-241.*

Jena and Gupta, Liquid Extrusion Techniques for Pore Structure Evaluation of Nonwovens, International Nonwovens Journal, vol. 12, No. 3. 2003, pp. 45-53.*

Jena and Gupta, Pore Structure Characteristics and Gas Permeability of Complete Filter Cartridges, Filtech 2005, p. 218-225.*

* cited by examiner

PORE STRUCTURE CHARACTERIZATION OF FILTRATION CARTRIDGES AT SPECIFIC LOCATIONS ALONG CARTRIDGE LENGTH

REFERENCE TO RELATED APPLICATIONS

This is a continuation-in-part patent application of co-pending application Ser. No. 12/558,865, filed Sep. 14, 2009, entitled "Determination of Pore Structure Characteristics of Filtration Cartridges as a Function of Cartridge Length", which is a divisional application of parent patent application Ser. No. 11/548,067, filed Oct. 10, 2006, now U.S. Pat. No. 7,614,279. The complete disclosures of the aforementioned applications are hereby incorporated herein by reference in their entireties.

BACKGROUND OF THE INVENTION

1. Field of the Invention

The invention pertains to the field of flow porometry. More particularly, the invention pertains to methods and apparatus for the use of flow porometry to determine the pore structure characteristics of a filtration cartridge from measurements taken at specific locations along the cartridge length.

2. Description of Related Art

Filtration cartridges are workhorses of modern industry. Filtration cartridges are porous materials widely used for the separation of suspended solids from liquids and/or gases. Numerous applications of filtration cartridges are found in a wide range of industries, including biotechnology, chemical, pharmaceutical, food and drink, medical, electronic, automobile, and the construction industries. A wide variety of tasks are performed by filtration cartridges, such as, for example, filtration of bacteria, pollen and cells from bodily fluids, purification of chemicals, detoxification of waste water, removal of heavy ions from water for use in the electronic industry, purification of pharmaceutical products, removal of pathogens and solids from soft drinks, and removal of excess water from slurries.

The performance of a filtration cartridge and its ability to separate solids from fluids are governed by the pore structure characteristics of the complete filtration cartridge, rather than just the pore structure of the filtration media contained therein. Analysis of the pore structure characteristics of filtration cartridges is required for the evaluation of numerous filtration processes, including, for example estimation of filtration efficiency, evaluation of cartridge performance, and development of advanced and more efficient filtration media. Relevant pore structure characteristics include, for example, through pore throat diameters, bubble point (i.e., the largest through pore throat diameter), mean flow pore diameter, pore distribution, and permeability. Through pore throat diameter determines the sizes of particles that will be prevented from passing through the pore. The bubble point is the largest through pore throat diameter; it determines the smallest particle that cannot pass through the filter. Mean flow pore diameter yields the mean value of the pore diameter. Normally the majority of pores have diameters close to the mean flow pore diameter. It is also a measure of liquid and gas permeability. Pore distribution shows where an appreciable fraction of pores is present. It can be used to estimate efficiency. Permeability is a measure of the rate of the process.

All of the foregoing properties, relevant and important for filtration, can be measured by Capillary Flow Porometry, based on ASTM F-316. Capillary flow porometry is widely used for pore structure determination of filtration media (see e.g., Akshaya Jena and Krishna Gupta, *Characterization of Pore Structure of Filtration Media*, Fluid/Particle Separation Journal, Vol. 14, No. 3, 2002, pp. 227-241; Akshaya Jena and Krishna Gupta, *Liquid Extrusion Techniques for Pore Structure Evaluation of Nonwovens*, International Nonwovens Journal, Vol. 12, No. 3. 2003, pp. 45-53; and U.S. Pat. Nos. 6,766,257 and 6,684,685, the complete disclosures of which are hereby incorporated herein by reference in their entireties).

U.S. Pat. No. 6,684,685 discloses a liquid extrusion porosimeter and method for evaluating porosity characteristics (specifically, pore volume, pore distribution and liquid permeability) of porous materials, such as filtration media. The porosimeter includes a fluid reservoir located below the sample, and a penetrometer comprising a vessel that catches any fluid displaced from the reservoir of fluid, wherein a level of fluid rises in the penetrometer when additional fluid enters the penetrometer. The sample is preferably wetted, with the same type of fluid that is in the reservoir, prior to placing the sample on the porosimeter. The porosimeter preferably also includes a membrane located between the sample and the reservoir of fluid. The membrane has pores with a size smaller than any of the sample pores. Pore volume of the sample is determined by measuring the change in fluid level in the penetrometer after pressure, which is above the bubble point pressure of the sample but below the bubble point pressure of the membrane, is applied to the sample. Permeability is measured by measuring rate of flow while the liquid level is above the sample.

The PMI Capillary Flow Porometer is a completely automated instrument. It measures pressures of the test gas accurately. It increases pressure in small increments, allows the system to equilibrate, and then records the increase in pressure. The flow rate through the sample is also measured accurately. Pressures can be raised to high values or reduced from high values to very low values. The porometer delivers the compressed gas through a tube to the sample chamber, which can be designed to hold samples of various sizes and shapes.

The technique of flow porometry is based on the simple principle that a wetting liquid spontaneously fills the pores of filtration media. For the wetting liquid, the surface free energy of the filtration media with the liquid is less than the surface free energy of the filtration media with air. Therefore, filling of the pores by the wetting liquid is accompanied by a decrease in free energy and the filling process is spontaneous. The wetting liquid cannot spontaneously flow out of the pores, however, it can be removed from the pores by a pressurized non-reacting gas.

The gas pressure needed to displace a wetting liquid from a pore is related to the pore diameter, as follows:

$$p = 4\gamma \cos \theta / D \tag{1}$$

where, p is the differential gas pressure on the wetting liquid in the pore, $\gamma$ is the surface tension of the wetting liquid, $\theta$ is the contact angle of the wetting liquid with the filtration media, and D is the pore diameter. The test involves measurement of gas flow rates through a dry sample as a function of differential pressure. The differential pressure is reduced to zero, the sample is wetted with a wetting liquid, and gas flow rates through the wet sample are measured as a function of differential pressure.

The wet curve generated by the wet sample shows no gas flow with increase in differential pressure at the beginning of the test, because all of the pores are filled with the wetting liquid. The first pore to be emptied at the lowest pressure is the largest pore (see Equation 1 above). The differential pressure that initiates gas flow through a wet sample yields the largest through pore diameter.

The diameter of a pore can change along the pore path. The differential gas pressure that is sufficient to displace liquid from the pore throat can completely empty the pore and initiate gas flow. Therefore, the pore diameter computed from the measured differential pressure yields the through pore throat diameter. The measured largest pore diameter is the largest through pore throat diameter. The dry curve is produced by the dry sample. The half-dry curve represents computed data that yield half of the gas flow rate through the dry sample at a given differential pressure. The differential pressure at which the wet curve and the half-dry curve have the same flow rates yields the mean flow through pore throat diameter. The mean flow pore diameter is such that half of the flow is through pores smaller than the mean flow pore and the rest of the flow is through pores larger than the mean flow pore. The ratio of flow rates through the wet sample and the dry sample also yields flow distribution over pore diameter. This distribution has been shown to be close to pore fraction distribution (See A. K. Jena and K. M. Gupta, *Pore Size Distribution in Porous Materials*, Proceedings of International Conference Filtration 99, November 3-4, Chicago, INDA, 1999). Gas permeability is computed from measured gas flow rates through the dry sample using Darcy's law (See P. C. Carman, *Flow of Gases through Porous Media*, Academic Press, 1956).

Characteristics of filtration media that can be measured accurately by flow porometry include, for example, the constricted pore diameter, the largest pore diameter, the mean flow pore diameter, pore distribution, gas permeability, liquid permeability, envelope surface area and effects of operational variables, such as temperature, pressure, chemical environment and stress. Demonstrated applications of flow porometry include analysis of pore characteristics in the thickness direction, pore characteristics in the x-y plane, properties of individual layers of multi-layered products determined in-situ without separating the layers, and evaluation of properties without cutting samples and damaging the products. See, e.g., U.S. Pat. Nos. 6,766,257, 6,789,410, 6,845,651, and 7,040,141.

U.S. Pat. No. 6,766,257 discloses a method of determining the pore structure of the individual layers in a multi-layered composite porous material, including the steps of providing a sample of a multi-layered porous material, sealing the sample in suitable test chamber, filling the pores of the sample material with a wetting liquid, such that the liquid/sample surface free energy is less than the gas/sample surface free energy, using a non-reacting gas to apply pressure to one side of the sample sealed in the test chamber, increasing the gas pressure gradually, so as to displace the liquid from the pores, increasing gas flow through the sample, measuring the pressure at which liquid flows from each successive layer of the sample material, and calculating the pore structure using an equation selected from the group consisting of $p=\gamma$ (dS/dV), $D=4\gamma/p$, and $f=-d[100(F_w/F_d)]/dD$.

U.S. Pat. No. 6,789,410 discloses a porosimeter that includes a pressurizable sample chamber with a membrane located directly below the sample. The membrane pores have a smaller size than any of the sample pores of interest. A fluid reservoir is located below the membrane such that the reservoir and the membrane form a seal. In operation, as fluid enters the fluid reservoir through the membrane or a reservoir inlet, fluid already in the fluid reservoir is displaced through a reservoir exit. An inlet in a fluid displacement reservoir receives the fluid displaced from the fluid reservoir. A recirculation line receives fluid from the exit of the fluid displacement reservoir and circulates the fluid into the inlet of the fluid reservoir. In a preferred embodiment, a pump recirculates the fluid through the recirculation line. Fluid returned to the reservoir circulates over the bottom of the membrane, and sweeps air bubbles out of the reservoir.

U.S. Pat. No. 6,845,651 discloses a method and apparatus for determining surface area and pore distribution of a sample. A pressurizable sample chamber of known volume holds a sample with unknown porosity characteristics. The sample chamber has a known pressure (or vacuum). A flow controller preferably controls the flow of the pure gas to be adsorbed by the sample in the sample chamber. A pressure monitor preferably monitors the pressure in the sample chamber. Once the pressure approaches a target pressure, the flow controller is closed. The pressure monitor continues to monitor the pressure until it stops changing when an equilibrium is attained. The amount of gas introduced into the system through the flow controller and the volume and final pressure of the sample chamber are used to calculate the amount of gas adsorbed. This calculation is subsequently used to determine the porosity characteristics of the sample. Some of these characteristics include, but are not limited to, pore distribution and surface area.

U.S. Pat. No. 7,040,141 discloses a method and apparatus for determining porosity characteristics of a sample having a plurality of pores, located within a pressurizable chamber. The sample divides the chamber into a first volume and a second volume. A known amount of vapor is introduced into the first volume and the second volume at the same pressure ($P_X$). After equilibrium is reached, pressure and decrease in volume of vapor are measured. Pore diameter and pore volume are calculated. A pressure differential is created between the two volumes, and the pressure change is monitored after the pressure differential is introduced. In a preferred embodiment, the pressure is increased in the first volume by a small percentage ($\Delta P_X$), and the pressure change on both sides of the sample is monitored after the pressure increase. The flow rate of the vapor is calculated using the pressure change. These steps are preferably repeated. The pore distribution in the sample is preferably calculated from the flow rates.

Although there are known methods and apparatus for the analysis of pore structure characteristics of filtration media, one problem with the known methods is that they are not well-suited for analyzing the pore structure characteristics of complete filtration cartridges. Determination of pore structure of porous materials by porometry involves measurement of differential pressure of an inert gas and the flow rate of the gas through the pores. However, large and long industrial cartridges produce very high gas flow rates. When flow rates are high, it is difficult to prevent turbulence, accurately measure flow rates, detect small changes in flow rates, and accurately measure small changes in differential pressure. Consequently, it is difficult to determine the pore structure of many large cartridges.

The known methods and apparatus do not allow the pore structure characteristics of a complete filtration cartridge to be determined from measurements taken at specific locations along the cartridge length, and do not allow the pore structure of the cartridge to be evaluated as a function of cartridge length. Thus, there is a need in the art for a method and apparatus for using flow porometry to determine the pore structure characteristics of complete filtration cartridges and evaluate pore structure at different locations along the length of the cartridge and as a function of cartridge length.

SUMMARY OF THE INVENTION

The present invention provides methods and apparatus for the use of flow porometry to determine the pore structure characteristics of a filtration cartridge from measurements taken at specific locations along the cartridge length. The apparatus according to the invention provides various porometry test location isolating devices designed for using a flow porometer to determine the pore structure characteristics at any location along the length of a filtration cartridge, including means for directing the flow of a pressurized test gas through a preselected test location along the length of the filtration cartridge. The test location isolating devices easily are operatively connected to a porometer to enhance its ability to determine pore structure characteristics of a cartridge as a function of its length. Various alternative embodiments include test location isolating devices provided as inserts, rings, and sleeves that slidingly engage either the inner or outer surface of the filtration cartridge and direct the test gas through the selected test location along the length of the cartridge.

One problem with determination of the pore structure of porous materials by porometry is that it involves measurement of differential pressure of an inert gas and the flow rate of the gas through the pores. However, large and long industrial cartridges produce very high gas flow rates. When flow rates are high, it is difficult to prevent turbulence, accurately measure flow rates, detect small changes in flow rates, and accurately measure small changes in differential pressure. Consequently it is difficult to determine the pore structure of large cartridges by porometry.

We have found that this problem can be avoided by performing the test on a small part of the cartridge. By controlling the size of the portion of the filtration cartridge on which the test is performed, it is possible to bring the flow rate under control. The test is repeated on neighboring parts to investigate the entire cartridge. This technique also permits investigation of the pore structure as a function of cartridge length, so that unusually large inhomogeneity can be identified and, if required, appropriate changes in the manufacturing process can be implemented. Several porometry test location isolating devices have been designed and used by Porous Materials, Inc. (see e.g., U.S. Pat. No. 7,614,279). We have recently developed two new pore structure isolating devices, which are very convenient to use to isolate test zones on large cartridges.

Briefly stated, a method according to the invention provides for determining the pore structure characteristics of a filtration cartridge, including the steps of placing a porometry test location isolating device in sealing contact with the filtration cartridge at a desired test location, increasing the porometer test gas pressure until the test gas flows through the cartridge at the test location, measuring the flow rate of the test gas through the test location as a function of differential pressure, reducing the test gas pressure to atmospheric pressure, wetting the test location with a wetting liquid, increasing the test gas pressure again until the test gas flows through the cartridge at the test location, measuring differential gas pressure and gas flow rates through the test location, and converting the measured gas flow rates and differential pressures into through pore throat diameters, largest through pore throat diameter, mean flow through pore throat diameter, pore distribution, and gas permeability of the cartridge. The methods and apparatus thus allow the use of flow porometry to determine the pore structure characteristics of a filtration cartridge from measurements taken at specific locations along the cartridge length.

In a preferred embodiment, the invention provides a porometry test location isolating device comprising a ring assembly adapted to slidingly engage the outer surface of a cylindrical filtration cartridge. There are three grooves on the inside surface of the ring and the cartridge moves freely inside the ring. Thus, when the ring is placed around the cartridge, a small space is left between the ring and the cartridge. The space is connected to the supply of a pressured test gas. The cylindrical ring member has a sealing groove within each end of an inner surface thereof, each groove defining a channel for receiving expandable circular sealing tubes. A central groove between the two sealing grooves defines a central gas channel arranged to direct flow of the test gas through the ring member to a preselected test location of the filtration cartridge. A test gas inlet provides the test gas to the central gas channel. The expandable circular sealing tubes are seated within each sealing groove. These sealing tubes define the test location and, when expanded, confine the flow of the pressurized test gas through the test location.

In an alternative embodiment, the invention provides a porometry test location isolating device comprising a ring assembly adapted to slidingly engage the outer surface of a cylindrical filtration cartridge. The ring assembly includes a cylindrical ring member having threaded ends for receiving a threaded cylindrical end piece at each end of the ring. An O-ring is sandwiched between each threaded cylindrical end piece and each threaded end of the ring member to create an air-tight seal. The assembly also includes a sealing groove for receiving multiple gaskets within each end of an inner surface of the ring assembly. Each sealing groove is defined by a recess within the inner side of each end piece and a corresponding recess within each end of the ring member. A central groove between the two sealing grooves defines a central gas channel arranged to direct flow of the test gas through the ring member to a preselected test location of the filtration cartridge. A test gas inlet provides the test gas to the central gas channel. Two or more gaskets of varying hardnesses and thicknesses are seated within each sealing groove. These gaskets define the test location and confine the flow of the pressurized test gas through the test location.

Thus, the invention allows the pore structure of a filtration cartridge to be determined by flow porometry at any location along the length of the cartridge, and allows the pore structure characteristics of the cartridge to be evaluated as a function of cartridge length. Furthermore, the invention provides means for employing a quick scan along the length of a cartridge as an aid in identifying the presence of major defects. The invention thus provides the advantage of enabling the use of flow porometry to determine the pore structure characteristics of a filtration cartridge from measurements taken at specific locations along the cartridge length. This is particularly useful for analysis of very large and/or high-flow industrial filtration cartridges.

These and other features and advantages will become readily apparent from the following detailed description, which should be read in conjunction with the accompanying drawing figures.

BRIEF DESCRIPTION OF THE DRAWINGS

The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF THE INVENTION

Figure 1:
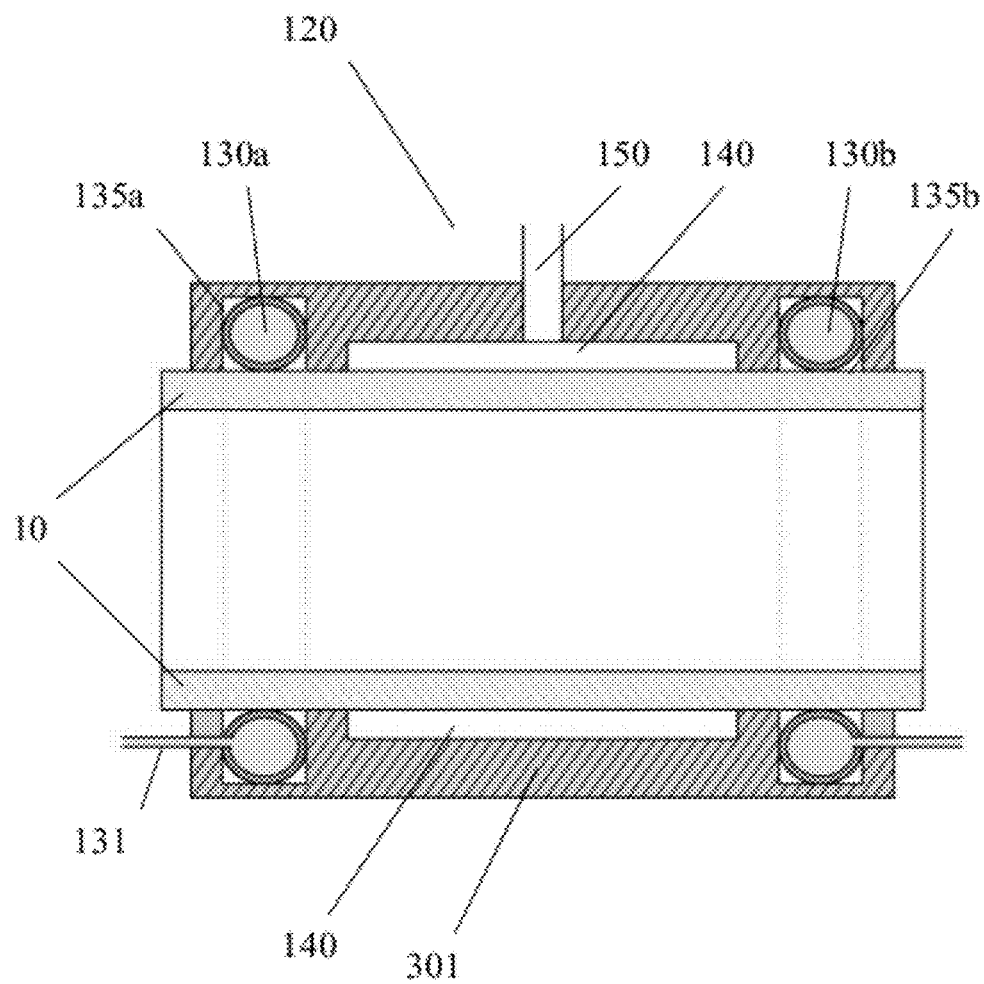
FIG. 1 depicts a cross-sectional view of a cylindrical ring assembly with expandable sealing tubes, in accordance with an embodiment of the invention.

The following description relates to certain preferred embodiments of apparatus and methods for using flow porometry to determine the pore structure characteristics of filtration cartridges as a function of cartridge length. It will be readily apparent that numerous variations and modifications other than those specifically indicated will be readily apparent to those of sufficient skill in the art. In addition, certain terms are used throughout the discussion in order to provide a convenient frame of reference with regard to the accompanying drawings, such as "inside", "outside", and the like. Such terms are not intended to be specifically limiting of the invention, except where so indicated in the claims.

Filtration cartridge product development ideally requires measurement of pore structure characteristics of complete filtration cartridges for design and performance evaluation. Important pore structure characteristics required for filtration cartridges include through-pore throat diameters, the bubble point pore diameter, mean flow pore diameter, and pore distribution. All of these characteristics can be measured by capillary flow porometry. However, testing of a complete filter cartridge by capillary flow porometry is a major challenge, because of the high gas flow rates through large cartridges, large size of the sample holder, need for accurate measurement of pressure drop, and requirement of sufficient supply of gas for a reasonable time.

The pore structure characteristic of an entire filter cartridge can be measured by a porometer, provided that the porometer is capable of accommodating the complete cartridge in the sample chamber, producing very high flow rates of gas for large cartridges, accurately measuring flow rates and pressure drops in such a system, and supplying adequate amount of gas for the test duration. The PMI Complete Filter Cartridge Analyzer has all of these features and we have recently shown that it is capable of measuring the relevant pore structure characteristics of an entire filtration cartridge (Akshaya Jena and Krishna Gupta, *Pore Structure Characteristics and Gas Permeability of Complete Filter Cartridges*, Proceedings, Filtech, Germany, Oct. 11-13, 2005).

Filter cartridges are often long, so that their output is high. The pore structure of a long cartridge normally is not uniform. Large size pores, increased or decreased concentration of pores, and defects produced during manufacturing due to factors such as non-uniform distribution of powders or fibers, non-uniform compaction, and improper sintering or hot pressing may be present at a number of locations along the length of a long cartridge. However, the presence of such structural abnormality is not usually revealed, when the entire cartridge is tested as a whole. Thus, the performance of a cartridge may be poor, even though the overall pore structure of the entire cartridge containing defects along its length appears to be satisfactory. It is, therefore, imperative to be able to measure the pore structure characteristics of a complete filtration cartridge at various locations along its length, to eliminate cartridges with unacceptable defects, and/or make changes in processing techniques used for the manufacture of the cartridges, so as to avoid or minimize such defects. However, due to the foregoing problems, currently available methods do not allow for the measurement of the pore structure characteristics of a complete filtration cartridge at various locations along its length.

In the present invention, we disclose novel apparatus and methods that have been developed to determine the pore structure at various locations along the length of a filtration cartridge, using a flow porometer (i.e., the PMI Capillary Flow Porometer). The methods and apparatus disclosed herein have been successfully used to measure various relevant characteristics of through pores, including throat diameters, largest throat diameter, mean flow pore throat diameter, pore distribution, and permeability.

The typical filtration cartridge is a hollow cylindrical shape with a porous wall and a cross-section that normally is circular. Fluids (liquid or gas) pass through the pores, while solid particles in the fluid are held back by the pores. The fluid moves either from the inside to the outside or from the outside to the inside of the cylinder.

In order to test a selected location on the cartridge, we devised methods and specialized apparatus to permit flow of the test gas only through a selected test location of the filter. These techniques generally involve the use of specially designed test location isolating devices, such as inserts, rings, or sleeves that slide either inside or outside the cartridge, several examples of which are described below. Different inserts can be used, depending upon the shape or configuration of the filtration cartridge being tested, such that the inserts substantially match the shape of the cartridge.

Referring now to FIG. 1, a porometry test location isolating device comprising a cylindrical ring assembly 120 with expandable circular sealing tubes 130a, 130b is shown, according to an embodiment of the present invention, specially adapted to slide over the outside of a cylindrical filtration cartridge 10. The apparatus includes a cylindrical ring member 301, which fits around a cylindrical filtration cartridge 10 (FIG. 1). The cartridge moves freely inside the ring. When the ring is placed around the cartridge a small clearance space is left between the ring and the cartridge. The space is connected to the supply of a pressured test gas. The cylindrical ring member 301 has a sealing groove 135a, 135b within each end of an inner surface thereof, each groove defining a channel for receiving an expandable circular sealing tube 130a, 130b. A central groove between the two sealing grooves defines a central gas channel 140 arranged to direct flow of the test gas through the ring member 301 to a preselected test location of the filtration cartridge 10. A test gas inlet 150 provides the test gas to the central gas channel 140. The expandable circular sealing tubes 130a, 130b are seated within each sealing groove 135a, 135b. Each sealing tube 130a, 130b includes an inflation port 131. These sealing tubes define the test location and, when expanded, confine the flow of the pressurized test gas through the test location.

Figure 2:
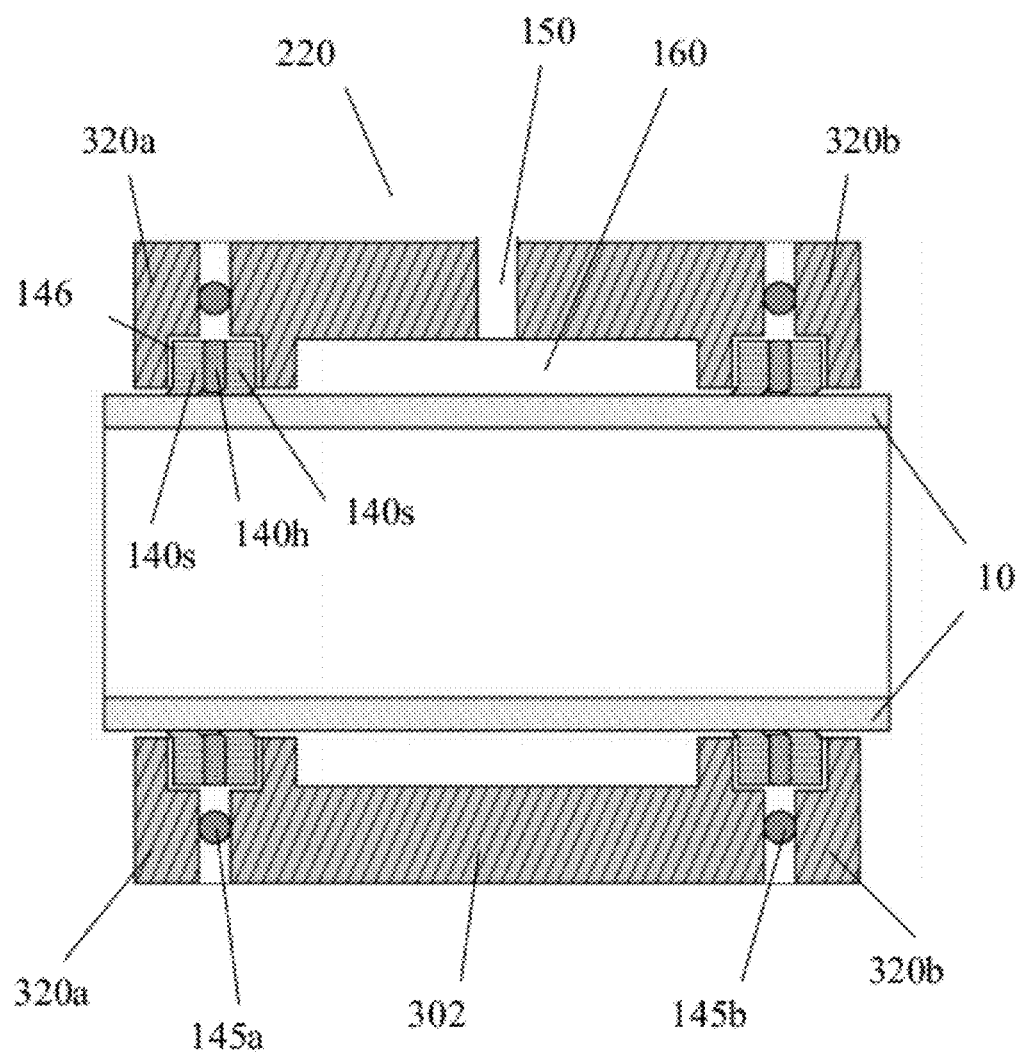
FIG. 2 depicts a cross-sectional view of a cylindrical ring assembly with hard and soft gaskets, in accordance with an embodiment of the invention.

Referring now to FIG. 2, a porometry test location isolating device comprising a cylindrical ring assembly 220 with hard and soft circular gaskets 140h, 140s is shown, according to an embodiment of the present invention, specially adapted to slide over the outside of a cylindrical filtration cartridge. The cylindrical ring member 302 used in this device has two relatively thin cylindrical end pieces 320a, 320b screwed to the ring member 302 with O-rings 145a, 145b in between to form air-tight seals (FIG. 2). The inner side of each end piece 320a, 320b has a recess 146 to accept two gaskets. The gaskets preferably are fixed to the end pieces with screws. Out of the two gaskets, one gasket is thin and flexible 140s while the other is hard and rigid 140h. On the side of the ring through which the cartridge is introduced, the thinner gaskets is on the outside while on the other side of the ring the thinner gaskets is on the inside. Optionally, two thinner gaskets are used for a better seal. When the cartridge is pushed in to the ring, the thinner gaskets are positioned in between the cartridge and the rigid gaskets, thus preventing leakage of the test gas to the outside of the ring (FIG. 2). A central groove between the two sealing grooves defines a central gas channel 160 arranged to direct flow of the test gas through the ring member 302 to a preselected test location of the filtration cartridge 10. A test gas inlet 150 provides the test gas to the central gas channel 160. The sealing gaskets define the test location and, confine the flow of the pressurized test gas through the test location.

The porometer is connected to the assembly of cartridge and the test location isolating device, such as the ring assembly. The test location isolating device is moved either manually or automatically by the porometer to the desired location. The porometer increases the pressure of the test gas in small increments. The gas is constrained to flow through the pores in the wall of the cartridge at the desired location. Gas flow rate through the selected part of the cartridge is measured as a function of differential pressure. The gas pressure is then reduced to atmospheric pressure, the test area is wetted with a wetting liquid, and gas pressure is slowly increased. Differential gas pressure and gas flow rates through the wet location are measured. The measured gas flow rates and differential pressures are converted into through pore throat diameters, the largest through pore throat diameter, mean flow through pore throat diameter, pore distribution, and gas permeability of the selected annular location on the cartridge wall. Pore structure characteristics at different locations are determined by moving the test location isolating device to the desired location. The pore structure characteristics of the cartridge as a function of its length can be determined by performing tests at locations with increasing length. Any sudden variation in the pore structure may be obtained by measuring flow rate as a function of length.

Examples of Successful Application of the Invention

The invention was used to determine the pore structure characteristics of a long cartridge at different locations along its length. It had a wall thickness of about 3/16th inch.

The fully automated PMI Capillary Flow Porometer was used to supply compressed gas to the apparatus and acquire the required data. The wetting liquid Galwick® (Propene, 1,1,2,3,3,3-hexafluro oxidized, polymerized) was used to wet the cartridge. The measured flow rates through the part of the cartridge at its center in dry and wet conditions were measured and reported as dry curve and wet curve respectively. The half-dry curve is computed to yield half of the flow rate through the dry sample at the same differential pressure.

Using these experimental data and using the procedure described above, the porometer computed the largest through pore throat diameter and the mean flow through pore throat diameter as 227.6 μm and 30.62 μm respectively in the center of the length of the cartridge. The pore distribution is given in terms of the distribution function, f, as follows:

$$f = -[d(F_w/F_d) \times 100]/dD \qquad (2)$$

where $F_w$ and $F_d$ are gas flow through wet and dry samples respectively. The distribution curve was calculated. The distribution function is such that area under the function in any pore size range yields percentage gas flow through pores in that range. The pore distribution is close to the pore number distribution.

Dry curve gave the gas flow rates through the dry sample. These flow rates were utilized to compute gas permeability of the sample using Darcy's law.

Thus, all of the important pore structure characteristics at the center of the length of the cartridge were measured and pore structures in other locations also were measured. Pore structures in this cartridge changed appreciably with length of the cartridge. For example, the mean flow through pore throat diameters at the two ends of the cartridge were 5.9% and 12.5% lower than the mean flow through pore throat diameter in the center.

Example I

The Cylindrical Ring with Expandable Tubes

The apparatus includes a cylindrical ring member 301, which fits around a cylindrical filtration cartridge 10 (FIG. 1). The cartridge moves freely inside the ring. When the ring is placed around the cartridge a small clearance space is left between the ring and the cartridge. The space is connected to the supply of a pressured test gas. The cylindrical ring member 301 has a sealing groove 135*a*, 135*b* within each end of an inner surface thereof, each groove defining a channel for receiving an expandable circular sealing tube 130*a*, 130*b*. A central groove between the two sealing grooves defines a central gas channel 140 arranged to direct flow of the test gas through the ring member 301 to a preselected test location of the filtration cartridge 10. A test gas inlet 150 provides the test gas to the central gas channel 140. The expandable circular sealing tubes 130*a*, 130*b* are seated within each sealing groove 135*a*, 135*b*. Each sealing tube 130*a*, 130*b* includes an inflation port 131 connected to the supply of air whose pressure is controlled. These sealing tubes define the test location and, when expanded, confine the flow of the pressurized test gas through the test location.

In order to perform a test the following procedure is followed:

1. The cylindrical ring is moved over the location of the cartridge selected for testing.
2. Air pressure in the sealing tubes is increased sufficiently to form air-tight seals between the sealing tubes and the cartridge.
3. Test gas is permitted to enter the space between the ring and the cartridge.
4. Flow rate of the test gas through the dry cartridge location between the two tubes is measured as a function of differential gas pressure.
5. The sealing tubes are deflated by reducing air pressure in the tubes.
6. The location of the cartridge between the tubes is carefully marked. The cartridge is withdrawn and wetted with a wetting liquid, such that all the pores of the cartridge at the selected location are filled with the wetting liquid.
7. The cylindrical ring is moved over the selected location of the cartridge and air pressure in the sealing tubes is increased to obtain air-tight seals between the cartridge and the tubes.
8. Test gas is permitted to enter the space between the ring and the cartridge.
9. Flow rate of the gas through the wet cartridge location between the two tubes is measured as a function of differential pressure of gas.
10. Using the measured flow and differential pressure values of wet and dry samples, the pore structure characteristics, such as bubble point, mean flow pore diameter, pore distribution, gas permeability and pore throat diameters are computed.
11. The sealing tubes are deflated by reducing air pressure in the tubes.
12. The cylindrical ring, which can now move freely over the cartridge, is relocated on another location of the cartridge, where the pore structure is required to be measured.

The unique advantages of this technique are many. For example, pneumatic pressure in the flexible tubes can be increased to the desired level to achieve a good seal with the cartridge surface. Cartridges having a wide range of pore diameters from very large (low test pressure) to very large (high test pressure) can be tested. The ring assembly easily can be mounted, removed or moved to a different location, simply by deflating the tubes. Also, cartridges having slightly irregular cross-section can be investigated Example II The Cylindrical Ring with Hard and Soft Gaskets The apparatus includes a cylindrical ring member 302 with two relatively thin cylindrical end pieces 320a, 320b screwed to the ring member 302 with O-rings 145a, 145b in between to form airtight seals (FIG. 2). The inner side of each end piece 320a, 320b has a recess 146 to accept two gaskets. The gaskets preferably are fixed to the end pieces with screws. Out of the two gaskets, one gasket is thin and flexible 140s while the other is hard and rigid 140h. On the side of the ring through which the cartridge is introduced, the thinner gaskets is on the outside while on the other side of the ring the thinner gaskets is on the inside. Optionally, two thinner gaskets are used for a better seal. When the cartridge is pushed in to the ring, the thinner gaskets are positioned in between the cartridge and the rigid gaskets, thus preventing leakage of the test gas to the outside of the ring (FIG. 2). A central groove between the two sealing grooves defines a central gas channel 160 arranged to direct flow of the test gas through the ring member 302 to a preselected test location of the filtration cartridge 10. A test gas inlet 150 provides the test gas to the central gas channel 160. The sealing gaskets define the test location and, confine the flow of the pressurized test gas through the test location.

In order to perform a test the following procedure is followed:
1. The cartridge is simply pushed from one side of the ring assembly, such that the ring is over the location of the cartridge selected for testing.
2. Test gas is permitted to enter the space between the ring and the cartridge.
3. Flow rate of the test gas through the dry cartridge location between the sealing gaskets is measured as a function of differential gas pressure.
4. The location of the cartridge between the gaskets is carefully marked. The cartridge is withdrawn and wetted with a wetting liquid such that all the pores of the cartridge at the selected location are filled with the wetting liquid.
5. The cylindrical ring is moved over the selected location of the cartridge and test gas is permitted to enter the space between the ring and the cartridge.
6. Flow rate of the gas through the wet cartridge location between the gaskets is measured as a function of differential pressure of gas.
7. Using the measured flow and differential pressure values of wet and dry samples, the pore structure characteristics, such as bubble point, mean flow pore diameter, pore distribution, gas permeability, pore throat diameters are computed.
8. The cylindrical ring is relocated on another location of the cartridge, where the pore structure is required to be measured.

The unique advantages of this technique are many. For example, the thickness and stiffness of the gaskets, as well as the number of gaskets used, can be adjusted to achieve a good seal with the cartridge surface. Cartridges having large pores requiring low test pressures are very suitable for this application. The ring assembly easily can be mounted, removed or moved to a different location, simply by pushing the cartridge. Also, cartridges having slightly irregular cross-section can be investigated.

The present invention thus provides the advantage of enabling the analysis of the pore structure characteristics of filtration cartridges to be determined by flow porometry at any location along the length of the cartridge, and allows the pore structure characteristics of the cartridge to be evaluated as a function of cartridge length. Furthermore, the invention provides means for employing a quick scan along the length of a cartridge as an aid in identifying the presence of major defects, and has numerous applications in the development and manufacture of filtration cartridges.

It is to be understood that the architectural and operational embodiments described herein are exemplary of a plurality of possible arrangements to provide the same (or equivalent) general features, characteristics, and general system operation. Therefore, while there have been described the currently preferred embodiments of the present invention, those skilled in the art will recognize that other and further modifications may be made, without departing from the spirit of the present invention, and it is intended to claim all modifications and variations as fall within the scope of the appended claims.

It must further be understood that the embodiments of the invention herein described are merely illustrative of the application of the principles of the invention. Reference to the details of the illustrated embodiments is not intended to limit the scope of the claims, which themselves recite the features regarded as essential to the invention.

What is claimed is:

1. Test apparatus for using a flow porometer to determine pore structure characteristics of at least a portion of a filtration cartridge, comprising a porometry test location isolating device having means for directing flow of a pressurized test gas through only a preselected test location along the length of said filtration cartridge, means for applying pressure in small increments to said test location, means for measuring differential pressures of said test gas, and means for measuring a rate of flow of said test gas through said test location, wherein said test location isolating device comprises a ring assembly adapted to slidingly engage an outer surface of a cylindrical filtration cartridge.

2. The apparatus of claim 1, wherein said ring assembly comprises:
  a) a cylindrical ring member having a sealing groove within each end of an inner surface thereof, each groove defining a channel for receiving expandable sealing means;
  b) a central groove between the sealing grooves, defining a central gas channel arranged to direct flow of said test gas through said ring member to said preselected test location of said cartridge;
  c) a test gas inlet for providing said test gas to said central gas channel; and
  d) expandable sealing means seated within each sealing groove, said sealing means defining said test location and, when expanded, confining flow of said pressurized test gas through said test location.

3. The apparatus of claim 1, wherein said ring assembly comprises:
  a) a cylindrical ring member having threaded ends for receiving a threaded cylindrical end piece at each end thereof;
  b) an O-ring sandwiched between each threaded cylindrical end piece and each threaded end of said ring member;

c) a sealing groove for receiving a plurality of gaskets within each end of an inner surface of said ring assembly, each sealing groove being defined by a recess within the inner side of each end piece and a corresponding recess within each end of said ring member;

d) a central groove between the sealing grooves, defining a central gas channel arranged to direct flow of said test gas through said ring member to said preselected test location of said cartridge;

e) a test gas inlet for providing said test gas to said central gas channel; and f) two or more gaskets of varying hardnesses and thicknesses seated within each sealing groove, said gaskets defining said test location and confining flow of said pressurized test gas through said test location.

4. The apparatus of claim 2, operatively connected to a flow porometer and/or means for manually or automatically moving said test location isolating device along the length of said filtration cartridge.

5. The apparatus of claim 3, operatively connected to a flow porometer and/or means for manually or automatically moving said test location isolating device along the length of said filtration cartridge.

6. A method for using a flow porometer to determine pore structure characteristics of at least a portion of a filtration cartridge, comprising the steps of:

a) providing a flow porometer and a filtration cartridge for analysis;

b) placing a porometry test location isolating device of claim 2 in sealing contact with said filtration cartridge at a preselected test location of said cartridge;

c) expanding said sealing means and increasing a test gas pressure of said porometer incrementally, such that said test gas is constrained to flow through said filtration cartridge at said test location;

d) measuring a flow rate of said test gas through said test location as a function of differential pressure;

e) reducing said test gas pressure to atmospheric pressure;

f) wetting said test location with a wetting liquid;

g) increasing said test gas pressure again incrementally, such that said wetting liquid is constrained to flow through said filtration cartridge at said test location;

h) measuring differential gas pressure and gas flow rates through said test location; and i) converting said measured gas flow rates and differential pressures into through pore throat diameters, the largest through pore throat diameter, mean flow through pore throat diameter, pore distribution, and gas permeability of said filtration cartridge at said test location.

7. The method of claim 6, further comprising the step of determining pore structure characteristics at different test locations along the length of said filtration cartridge by moving said test location isolating device to multiple test locations, measuring flow rates and differential pressures at said multiple locations, and converting said measured gas flow rates and differential pressures at said multiple test locations.

8. The method of claim 6, further comprising the step of determining pore structure characteristics of said filtration cartridge as a function of its length by performing tests at locations with increasing length.

9. The method of claim 6, further comprising the step of determining variation in pore structure by measuring flow rate as a function of length.

10. The method of claim 6, wherein said test location isolating device is moved to said multiple test locations manually or automatically by said flow porometer.

11. The method of claim 6, comprising the step of determining said pore structure characteristics using the formula $p=4\gamma \cos\theta/D$ or $f=-[d(F_w/F_d)\times 100]/dD$.

12. A method for using a flow porometer to determine pore structure characteristics of at least a portion of a filtration cartridge, comprising the steps of:

a) providing a flow porometer and a filtration cartridge for analysis;

b) placing a porometry test location isolating device of claim 3 in sealing contact with said filtration cartridge at a preselected test location of said cartridge;

c) increasing a test gas pressure of said porometer incrementally, such that said test gas is constrained to flow through said filtration cartridge at said test location;

d) measuring a flow rate of said test gas through said test location as a function of differential pressure;

e) reducing said test gas pressure to atmospheric pressure;

f) wetting said test location with a wetting liquid;

g) increasing said test gas pressure again incrementally, such that said wetting liquid is constrained to flow through said filtration cartridge at said test location;

h) measuring differential gas pressure and gas flow rates through said test location; and i) converting said measured gas flow rates and differential pressures into through pore throat diameters, the largest through pore throat diameter, mean flow through pore throat diameter, pore distribution, and gas permeability of said filtration cartridge at said test location.

13. The method of claim 12, further comprising the step of determining pore structure characteristics at different test locations along the length of said filtration cartridge by moving said test location isolating device to multiple test locations, measuring flow rates and differential pressures at said multiple locations, and converting said measured gas flow rates and differential pressures at said multiple test locations.

14. The method of claim 12, further comprising the step of determining pore structure characteristics of said filtration cartridge as a function of its length by performing tests at locations with increasing length.

15. The method of claim 12, further comprising the step of determining variation in pore structure by measuring flow rate as a function of length.

16. The method of claim 12, wherein said test location isolating device is moved to said multiple test locations manually or automatically by said flow porometer.

17. The method of claim 12, comprising the step of determining said pore structure characteristics using the formula $p=4\gamma \cos\theta/D$ or $f=-[d(F_w/F_d)\times 100]/dD$.

* * * * *